United States Patent [19]

Hogg

[11] 3,973,196

[45] Aug. 3, 1976

[54] METHOD AND APPARATUS FOR EJECTING A METERED AMOUNT OF PARTICULATE SAMPLE

[75] Inventor: Walter R. Hogg, Miami Lakes, Fla.

[73] Assignee: Coulter Electronics, Inc., Hialeah, Fla.

[22] Filed: June 5, 1975

[21] Appl. No.: 584,142

Related U.S. Application Data

[63] Continuation-in-part of Ser. No. 473,127, May 24, 1974, Pat. No. 3,890,569.

[52] U.S. Cl. .......................... 324/71 CP; 73/432 PS
[51] Int. Cl.² ........................................ G01N 27/00
[58] Field of Search .............. 324/71 CP; 73/432 PS

[56] References Cited
UNITED STATES PATENTS

| | | | |
|---|---|---|---|
| 3,165,693 | 1/1965 | Isreeli et al. ..................... | 324/71 CP |
| 3,810,010 | 5/1974 | Thom............................. | 324/71 CP |
| 3,871,770 | 3/1975 | von Behrens et al. ....... | 324/71 CP X |

FOREIGN PATENTS OR APPLICATIONS

| | | | |
|---|---|---|---|
| 2,042,474 | 3/1972 | Germany ........................ | 324/71 CP |

*Primary Examiner*—John K. Corbin
*Assistant Examiner*—R. Hille
*Attorney, Agent, or Firm*—Silverman & Cass, Ltd.

[57] ABSTRACT

A particle study device wherein a non-diluted specific minute amount of fluid sample containing particles is ejected by an ejecting mechanism into a flow stream leading to a sensing zone in the particle study device. The ejecting mechanism includes a hollow body having a thermal expansion device mounted therein. The temperature of the thermal expansion device is monitored and stored. The device operation then is initiated and power is supplied to the thermal expansion device to raise its temperature and cause it to expand thereby to eject from the hollow body a fluid sample. The temperature rise of the thermal expansion device is monitored and when a predetermined temperature rise has occurred indicating ejection of a specific amount of fluid sample, the power supplied to the thermal expansion device is terminated thus terminating further temperature rise and expansion.

22 Claims, 3 Drawing Figures

METHOD AND APPARATUS FOR EJECTING A METERED AMOUNT OF PARTICULATE SAMPLE

CROSS REFERENCE TO RELATED APPLICATIONS

This application is a Continuation-in-Part of U.S. patent application Ser. No. 473,127 filed May 24, 1974, now U.S. Pat. No. 3,890,569, and is related to U.S. Pat. No. 3,859,012, which is to be considered incorporated by reference herein to the extent required. Both the above noted patent application and patent are owned by the same Assignee as this application.

BACKGROUND OF THE INVENTION

The invention relates to a non-diluting particle study device and more specifically to a device for ejecting a non-diluted specific minute amount of fluid sample containing particles into a flow stream leading to a sensing zone in the particle study device.

Heretofore, in the field of particle analysis and particle study, such as the study of red and white blood cells in a blood sample, it has been common practice to dilute the blood sample and then to pass a portion of the diluted sample through a sensing zone in a particle study device. The blood is diluted because the normal human blood count is five million cells per cubic millimeter and it is only necessary to study or analyze one hundredth of that amount, namely, a volume of 0.01 cubic millimeters.

In studying a blood sample, the blood cells in a given amount of the sample are counted by passing a portion of the diluted blood sample through a sensing zone in a particle analyzing device, such as a Coulter type particle analyzing device which operates on the Coulter sensing principle disclosed in U.S. Pat. No. 2,656,508 issued Oct. 20, 1953 to Wallace H. Coulter.

According to this principle, when a microscopic particle in suspension in a fluid electrolyte is passed through an electrical field of small dimensions approaching those of the particle, there will be a momentary change in the electric impedance of the electrolyte in the ambit of the field. This change of impedance diverts some of the excitation energy into associated electrical circuitry, giving rise to an electrical signal. Such signal has been accepted as a reasonably accurate indication of the particle volume for most biological and industrial purposes.

One apparatus of the Coulter type includes first and second vessels each containing a body of fluid electrolyte. The second vessel is smaller and is immersed in the electrolyte in the first vessel. An electrode extends into the electrolyte in each vessel and electric current flows between the electrode through an opening in the side wall of the second vessel, the opening consisting of a minute aperture commonly referred to as a Coulter aperture. Flow of liquid between the vessels is caused by applying vacuum to the second vessel. According to the Coulter principle, particles passing through the aperture from one body of electrolyte to the other body of electrolyte will change the impedance of the electrolyte contained within the aperture and this change in impedance is sensed by the electrodes. This change generates an electrical signal in the form of a particle pulse which is then counted by the electrical circuitry of the particle analyzing device.

When making a blood analysis a dilution of blood in electrolyte is placed in the first vessel. Then vacuum is applied to the second vessel to cause diluted blood to flow from the first vessel through the aperture into the second vessel for a specific period of time. The second vessel is filled with electrolyte, probably including prior dilutions.

To make a fairly accurate measurement of particle concentration, one must accurately measure or meter the amount of fluid which passes through the sensing zone during a period of time when the electrical circuitry of the device is operative. This can be accomplished by passing fluid through the sensing zone at a given flow rate for a specified period of time. Apparatus utilizing fluid flow metering systems of this type in a fluid analyzing device are disclosed in U.S. Pat. Nos. 3,577,162 and 3,654,439.

In most Coulter type particle analyzing devices, the metering is accomplished with a fluid metering apparatus of the type disclosed in U.S. Pat. Nos. 2,869,078, 3,015,775 and 3,271,672. Such metering apparatus includes a closed fluid system hydraulically connected to the second vessel. The closed fluid system includes a connection to a vacuum source and a mercury manometer. When operating the device, vacuum is applied to the closed fluid system to raise the mercury in the manometer and to draw some fluid sample into the second vessel. The connection to the vacuum source is then closed and the manometer, by reason of the mercury flowing downwardly to its original position, causes liquid to be drawn through the aperture and generates signals indicating the beginning and the end of an analytic run in a period during which an accurately metered volume of fluid is passed through the aperture. The metered volume of fluid is equal to the volume within the manometer between two electrodes.

It will be understood from the foregoing description of a Coulter type particle analyzing device that it is necessary to dilute a quantity of blood, to make an accurate determination of dilution and to accurately meter the fluid flow through the Coulter aperture in order that an accurate count of blood cells can be made. A simpler way of making the particle analysis or study would be to pass a specific minute amount of undiluted blood through the Coulter aperture and thereby eliminate the manometer and diluter systems. A device for ejecting a specific minute amount of particle-containing fluid such as blood into the flow stream leading to a sensing zone in a particle analyzing device is shown in the Parent Patent Application Ser. No. 473,127 filed May 24, 1974 and U.S. Pat. No. 3,859,012.

In both the above noted patent application and patent, circuitry is disclosed for operating the ejecting device. The circuitry provides a predetermined amount of electrical energy to the device causing it to increase in temperature, expand and eject a specific amount of fluid. The amount of energy provided is determined mathematically and, in the embodiment described therein, is the amount of energy necessary to raise the temperature of the device twenty degrees, a twenty degree rise causing a specific expansion and therefore an ejection of a specific amount of fluid.

If sufficient thermal insulation is used to ensure that heat loss during a heating cycle is negligible so that all the energy supplied is stored as heat in the expansive element an extended cool-off period is desirable. Extended cool-off periods are undesirable from an operational point of view. On the other hand, if the insulation is designed to permit rapid cool-off, the heat loss during the expansion period must be taken account of and compensated for. This is unsatisfactory because neither the temperature gradient across the insulation nor the ambient temperature are fixed and/or well known quantities. Consequently, it would be preferable to measure temperature rise within the ejecting device rather than the specific amount of supplied energy.

SUMMARY OF THE INVENTION

In practicing this invention, a particle study device is provided which has an ejecting device that includes means for receiving and temporarily storing a given amount of sample and a thermal expansion device mounted within the receiving and storing means. A source of energy is coupled to the thermal expansion device to raise the temperature of the expansion device and cause the device to expand and increase in volume thereby ejecting an amount of sample from the receiving and storing device. First means are contained within the thermal expansion device and have a characteristic which varies with temperature for allowing monitoring of the device temperature. Second circuitry is coupled to the first means and to the energy supply and is operative in response to the first means characteristic varying by a predetermined amount, thus indicating a variation in temperature of a predetermined amount and a resulting expansion of a predetermined amount to terminate the supply of energy to the thermal expansion device thus terminating expansion whereby a predetermined specific amount of sample is ejected from said device.

In practicing this invention, the system for operating the ejection device noted above as explained above is also contemplated as being within the scope of this invention. Furthermore, the method of monitoring the temperature rise of the thermal expansion device within the ejecting device so as to allow only a predetermined temperature rise and therefore ejection of a specific amount of sample, is also contemplated as being within the scope of this invention.

DESCRIPTION OF THE PREFERRED EMBODIMENTS

Figure 1:
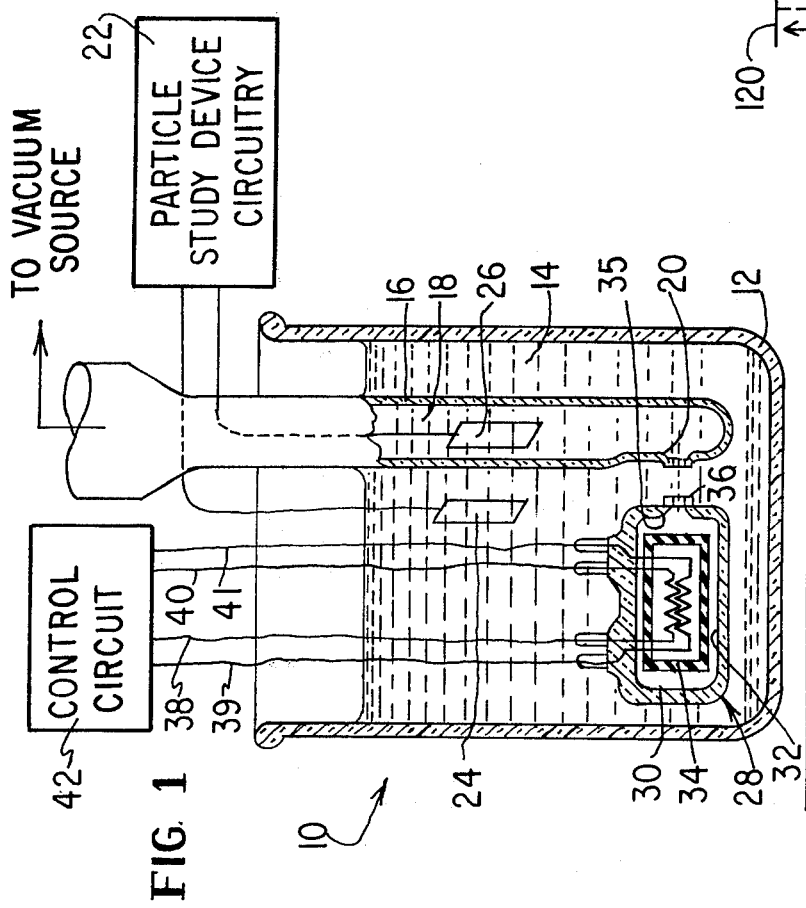
FIG. 1 is a diagrammatic view of a particle study device including a vertical sectional view of a sensing zone in the device and a portion of an ejecting mechanism of the present invention positioned adjacent the sensing zone.

A particle study device generally of the Coulter type is identified by the reference numeral 10 in FIG. 1. The device 10 includes a first vessel 12 having a body of fluid 14 therein. A second and smaller vessel 16 is situated within the vessel 12 with the lower portion of the vessel 16 immersed in the fluid 14. Preferably, and as shown, the vessel 16 is in the form of a tube which contains a body of fluid 18. Such a tube is known as an aperture tube and has an aperture in the side wall thereof, the aperture being formed in a wafer 20 secured to the side wall of the aperture tube 16 over an opening in the aperture tube 16. One type of wafer construction and mounting is disclosed in U.S. Pat. No. 2,985,830.

As indicated, the upper end of the aperture tube 16 is connected to a conventional vacuum source (not shown) which includes a control mechanism operable to connect the tube 16 to the vacuum source for a predetermined period of time. The control mechanism also controls the operation of the circuitry of the particle study device 10, which circuitry is generally indicated by reference numeral 22. The circuitry 22 includes lead connections to two electrodes 24 and 26 which are situated, respectively, in the bodies of fluid 14 and 18. An electric current flows between the electrodes through the aperture in the wafer 20. When vacuum is applied to the aperture tube 16 a portion of the fluid 14 is drawn through the aperture into the tube 16.

In a conventional Coulter particle study device the body of fluid 14 comprises a dilution of blood in an electrolyte such that diluted blood is drawn through the aperture. Particles such as blood cells in the blood passing through the aperture will change the impedance of the electrolyte in the aperture. This change in impedance is sensed by the circuitry 22 which generates an electrical signal, commonly referred to as a particle pulse, each time a particle passes through the aperture. The particle pulses produced in this manner are studied, analyzed, and/or counted by the circuitry 22.

In accordance with the teachings of the present invention the body of fluid 14 is pure electrolyte and does not contain particles, such as would be the case in a conventional apparatus. Instead of placing a diluted sample in vessel 12 to comprise the body of fluid 14, the particle study device 10 of the present invention includes an ejecting mechanism 28 for ejecting fluid sample into a pure body of electrolyte. As will be explained in detail hereinafter the ejecting mechanism 28 is operable to eject a specific minute amount of undiluted fluid sample suspension toward the aperture in the wafer 20. In this way the particle study device 10 is a non-diluting particle study device.

The ejecting mechanism 28 includes a hollow body 30 having a cavity 32 therein. A thermal expansion device 34 is situated in the cavity 32. As shown, one side wall of the body 30 has an opening 35 therein communicating with the cavity 32. The opening 35 is covered by a wafer 36 similar to the wafer 20. The wafer has an aperture therein forming an outlet orifice for the ejecting mechanism 28. This outlet orifice is preferably very small to minimize the mixing of the sample and electrolyte in and around it. The actual size of the aperture forming the outlet orifice is not critical and it is contemplated that wafers with apertures not meeting established standards for a Coulter type particle analyzing device can be used in the ejecting mechanism of the invention. As a result, rejected wafers can be salvaged and utilized in the ejecting mechanism of the present invention. A typical wafer will be one having an aperture of the order of $30\mu$.

The thermal expansion device 34 is connected via leads 38, 39, 40 and 41 to a control circuit 42 of the ejecting mechanism 28. The control circuit 42 includes a source of electric energy and circuitry for controlling the delivery of energy to the thermal expansion device 34 so that only the requisite amount of electrical energy is supplied to the device 34 to produce a predetermined increase in temperature of the device 34 and thereby cause a predetermined incremental increase in the volume of the device 34. It will be understood that when the device 34 is heated, it expands-increases in volume. The expansion causes a minute amount of the fluid sample to be ejected through the outlet orifice in the wafer 36.

Figure 2:
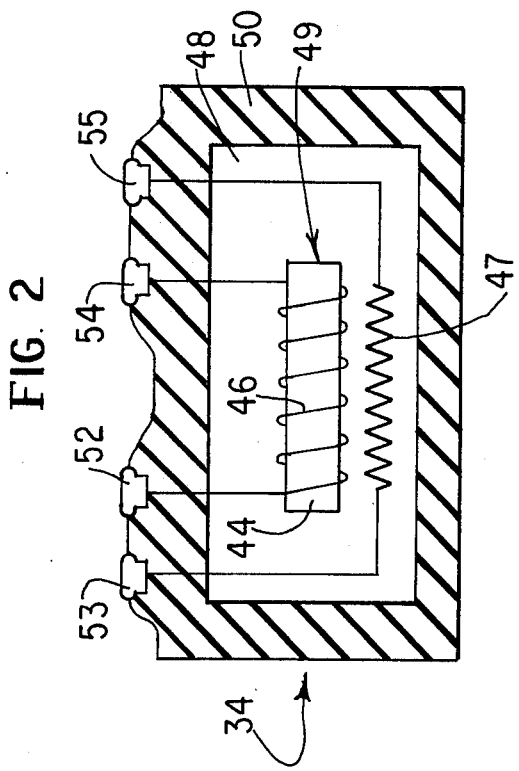
FIG. 2 is an enlarged view, particularly in section, of the thermal expansion device of the ejecting mechanism shown in FIG. 1.

As best shown in FIG. 2 the thermal expansion device 34 includes a core member 44 around which is wrapped a resistance element 46, namely, a wire conductor, which forms the heating element of the device 34. A thermistor 47 is positioned adjacent the core member 44. Thermistor 47 has a resistance which varies significantly with temperature. Core member 44, resistance element 46 and thermistor 47 are positioned in a body 48.

The core 44 and the body 48 form an expandable element generally identified by the reference numeral 49. Surrounding the body 48 is a slightly elastic but incompressible insulating jacket 50. As shown four electrical contacts or terminals 52, 53, 54 and 55 are fixed in the jacket 50. Terminals 52 and 54 are connected to the ends of the wire conductor 46, and terminals 53 and 55 are connected to the ends of thermistor 47. It will be understood that the leads 38, 39, 40 and 41 extend to the body 30 and are connected to terminals or contacts fixed in the inner wall of the body 30 in position to engage the contacts 52 through 55 respectively.

Figure 3:
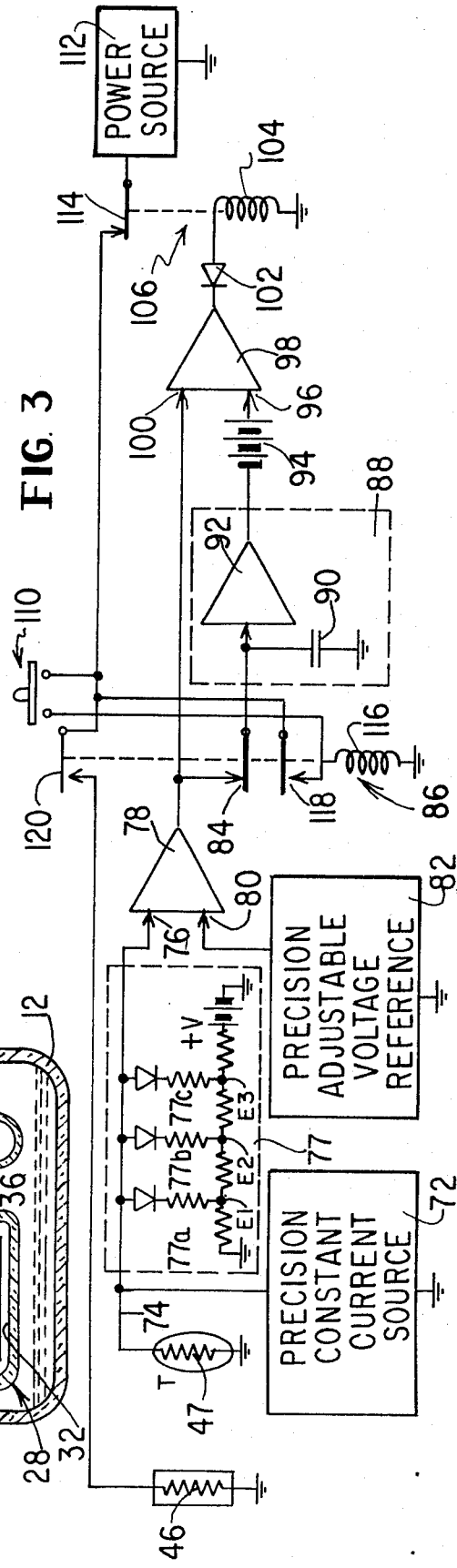
FIG. 3 is a schematic diagram of the ejecting mechanism and the system for operating the ejecting mechanism embodying the features of this invention.

The control circuit 42 for controlling the power supplied can take various forms. One such circuit is shown schematically in FIG. 3 and is generally identified by the reference numeral 70.

The circuit 70 includes a source of electrical power which is coupled to device 34 in order to supply energy for raising the temperature of device 34 and also includes control circuitry for measuring the temperature rise of the device 34 and supplying the power thereto only for a particular temperature rise. As noted previously, resistance element 46 and thermistor 47 are both positioned in body 48. Thermistor 47 in the preferred embodiment is a negative temperature coefficient thermistor. That is, it will have a particular resistance at a selected temperature, for example, of 25° centigrade. The resistance of thermistor 47 will decrease with an increase in the temperature above 25° centigrade and will increase with a decrease in temperature below the 25° centigrade level.

A precision constant current source 72 is connected between ground potential and one terminal 74 of thermistor 47, the other terminal of thermistor 47 being coupled to ground potential. Current source 72 supplies a small reference current to thermistor 47. The reference current is selected to be small enough so that the heat dissipated in thermistor 47 due to this current is negligible. The current from constant current source 72 will cause a voltage to be developed across thermistor 47. As the temperature change as a result of the current, and therefore the resistance change of thermistor 47 as a result of the current is negligible the resistance of thermistor 47 varies only with expansive element temperature and therefore the voltage developed thereacross is a function of the temperature of thermistor 47. As noted above, thermistor 47 has a negative temperature coefficient. The resistance of thermistor 47 may vary in a nonlinear manner with temperature. Consequently the voltage appearing at terminal 74 will vary in a nonlinear manner with temperature. The voltage appearing at terminal 74 of thermistor 47 is coupled to a nonlinear compensating network, shown within the dashed line block and identified by the numeral 77.

Nonlinear compensating network 77 is a diode resistor network of the type well known in the art, for compensating the nonlinearity of thermistor or other nonlinear device on a point-by-point basis. In the embodiment shown three compensation points are employed although as many as desired may be provided. Each diode resistor path represented by the numbers 77a, 77b and 77c will be rendered conductive when the voltage developed across thermistor 47 exceeds the voltages E, $E_2$ and $E_3$ respectively developed at the junction points shown. When a path is rendered conductive it will divert a portion of the current from thermistor 47 thus lowering the voltage thereacross. Greater reductions will occur for conduction of paths 77b and 77c than for conduction of path 77a producing greater voltage decreases at lower temperatures and higher voltages. This then compensates for the nonlinear increasing voltage across the thermistor at lower temperatures.

It should be noted that thermistors with resistance variations that are linear over particular temperature ranges are available. If such thermistors are employed nonlinear compensation network 77 should be deleted. The compensated voltage developed at compensation network 77 is coupled to one input 76 of a differential amplifier 78. The second input 80 of differential amplifier 78 is coupled to a precision adjustable voltage reference 82.

Precision adjustable voltage reference 82 is adjusted such that the voltage coupled to input 80 of differential amplifier 78 is slightly greater than the highest voltage to be expected at input 76 thus corresponding to a temperature slightly lower than the lowest temperature probable for thermistor 47. Differential amplifier 78 develops an output signal which is proportional to the difference between the two voltages at input terminals 78 and 80 respectively. As one voltage input represents a low reference temperature and the other input is proportional to the instantaneous temperature of thermistor 47 the voltage output of differential amplifier 78 is proportional to the difference between the low reference temperature and the instantaneous temperature of thermistor 47 and will vary linearly in accordance with this difference. Any change in this voltage is hence proportional to the change in temperature of thermistor 47.

The output of differential amplifier 78 is coupled through normally closed contact 84 of relay 86 to a track and hold circuit shown within the dashed lines 88. Track and hold circuit 88 includes a capacitor 90 coupled between contact 84 and ground potential and an amplifier 92 coupled to the junction of capacitor 90 and contact 84. When contact 84 is closed, the voltage developed at the output of differential amplifier 78 is developed across capacitor 90. Capacitor 90 will follow any voltage coupled thereto and will retain the voltage developed thereacross when contact 84 of relay 86 is opened thus storing the voltage therein. Amplifier 92 is a unity gain high input impedance buffer amplifier to prevent leakage of charge from capacitor 90; the output voltage of amplifier 92 will be the same as the voltage developed across capacitor 90.

The voltage developed at the output of amplifier 92 also is a measure of the temperature of thermistor 47. This stored voltage is added to D.C. voltage provided by battery 94 which is in series between the output of amplifier 92 and one input 96 of a comparator 98 providing a total voltage at input 96 of comparator 98. Since the voltage at the output of amplifier 92 is linearly related to the thermistor temperature the D.C. voltage provided by battery 94 represents a particular resistance change or temperature change for thermistor 47 so that the total voltage at input 96 represents the current temperature plus a particular temperature differential. In the preferred embodiment battery 94 represents a temperature differential of 20 degrees so that the voltage at input 96 represents the instantaneous temperature of thermistor 47 when contacts 84 are opened plus 20°.

The second input 100 of amplifier 98 is coupled directly to the output of differential amplifier 78. With the D.C. voltage provided by battery 94, the voltage coupled to input 96 at this time is greater than the voltage coupled to input 100. Comparator 98 is selected such that it will not develop an output signal at its output until the voltage at input 100 exceeds the voltage at input 96.

The output of comparator 98 is coupled through rectifying diode 102 to a relay coil 104 of relay 106. Consequently, relay 106 will not be energized until such time as the voltage at input terminal 100 of comparator 98 exceeds the voltage at input terminal 96.

When a sample suspension has been trapped in cavity 32 of ejecting mechanism 28, operation of the entire particle study device may be initiated by actuating the circuitry 22 and 42. Actuation of control circuit 42 may be initiated by operation of pushbutton start switch 110 which couples voltage from power source 112 through the normally closed contact 114 of relay 106 to coil 116 of relay 86, thus actuating relay 86. Upon actuation, normally closed contact 84 will open causing the voltage developed across capacitor 90 prior to initiation to be maintained thereacross. Consequently, the voltage coupled to input 96 is linearly related to the temperature of thermistor 47 and therefore of body 48 just prior to initiation of operation. At the same time, normally open contact 118 of relay 86 will close providing a short circuit in parallel with switch 110 thus maintaining a current path between power source 112 and relay coil 116 for maintaining relay 86 in an activated state after release of pushbutton 110. Upon actuation of relay 86, normally opened contact 120 also closes, coupling power source 112 through contact 114 of relay 106 and contact 120 of relay 86 to resistance element 46 in thermal expansion device 34.

The power or energy supplied to resistance element 46 will cause element 46 to increase in temperature causing core member 44 and body 48 to increase in temperature and to expand. The increase in temperature of core member 44 and body 48 will be communicated to thermistor 47 causing it to increase in temperature and decrease in resistance. This decrease in resistance will result in a decrease in voltage developed at the junction 74 and coupled to input 76 of differential amplifier 78. Consequently, the voltage developed at the output of differential amplifier 78 will increase and will continue increasing linearly in accordance with the increase in temperature of the expandible element 49 and thermistor 47.

The voltage developed at the output of differential amplifier 78 is coupled directly to input 100 of comparator 98. As the temperature of the expandible element 49 as sensed by thermistor 47 increases, the voltage coupled to input 100 of comparator 98 will increase until such time as the voltage at input 100 exceeds the voltage at input 96 thus indicating that the temperature of expandible element 49 is 20° higher than at initiation of operation. When the voltage at input 100 exceeds the voltage at input 96, comparator 98 will develop an output signal which is coupled to relay coil 104 of relay 106, actuating relay 106. Upon actuation, normally closed contact 114 of relay 106 will open, breaking the voltage path between power source 112 and relay coil 116 and between power source 112 and resistance element 46. With the voltage path opened, relay 86 will deenergize, thus terminating the operating cycle of this system. With the voltage path to resistance element 46 open, the temperature increase within thermal expansion device 34 will terminate, thus terminating expansion of device 34 and ejection of sample suspension, so that only a precise amount of sample suspension is ejected. Until the ejection cycle is repeated next time, the temperature of the expandible element 49 and thermistor 47 will slowly and exponentially subside to the ambient temperature at a rate depending on the thermal insulation of insulating jacket 50.

In practicing the teachings of the present invention it is contemplated that the core member 44 of the thermal expansion device 34 will be formed of a high thermal-conducting material such as silver or beryllium oxide, the latter being preferred not only for economy, but to eliminate the need for electrical insulation. Also the material of the body 48 within which the core 44 is embedded is preferably made from beryllium oxide. The coefficient of thermal expansion of silver is 10.9 ($10^{-6}$) and the coefficient of thermal expansion for beryllium oxide is 5.3 ($10^{-6}$). As stated above it has been found that a sufficient quantitiy of blood for analysis and study of the cells in the blood is 0.01 cubic millimeters of blood. Assuming a temperature rise of 20°F for the sake of convenience and assuming that the expandible element 49 formed by the core member 44 in the body 48 is cylindrical having a length equal to twice its diameter mathematical calculations show that a silver expandible element would have to be roughly 0.085 inches in diameter and have a length of roughly 0.170 inches to obtain an increase in volume of roughly 0.01 cubic millimeters for a 20°F increase in temperature of the expandible element. This is a very convenient size in that it does not require a large syringe. A small syringe can be utilized and a very small amount of blood sample is needed. Also the syringe and the thermal expansion device 34 are large enough so that they can be readily made utilizing the techniques used in manufacturing miniature resistors.

If a solid beryllium oxide (BeO) cylindrical expandable element is used instead of silver, the volume of the expandable element 49 should be roughly twice the volume of a silver expandable element. In this case, the diameter of the expandable element would be roughly 0.103 inches and the length of the element would be roughly 0.217 inches.

Rough calculations show that an expandable element made from BeO would require 1.09 calories of heat or 4.56 joules of energy in order to obtain an increase of 0.01 cubic millimeters in the volume of the element, if a temperature rise time of 20 seconds is assumed, and that power would have to be expended in the expandable element at the average rate of 0.228 watts.

One of the advantages obtained with a non-diluting particle counter utilizing the ejecting mechanism 28 heretofore described is the fact that much more electrolyte is sucked through the aperture in the wafer 20 than blood. The net effect is exactly the same as if the blood had been diluted. However, dilution does not matter since all the cells in the 0.01 cubic millimeter of blood ejected into the body of electrolyte 14 are to be counted.

The electrolyte being drawn through the aperture in the wafer 20 also serves as a sheath for the blood cells which flow through the aperture. By ejecting the specific minute amount of blood into the fluid adjacent the wafer 20 and being drawn through the aperture, essentially all of the blood cells are ensheathed by electrolyte and drawn through the aperture. As a result, practically none of the blood cells will be lost in the electrolyte.

Modifications and variations to the system heretofore described will be apparent to those skilled in the art. For instance, the relays 106 and 86, while lending themselves to a simple, clear explanation of the operation of the invention, could be replaced by semiconductor circuits. The battery 94 could be replaced with an operational amplifier circuit, well known in the art, for causing the sum of two ground-referenced voltages to appear on terminal 96. The invention would also work in the environment of an optical particle counter and in other fields. Adjustment means could easily be added to the voltage offset provided by the battery 94 to control the amount of sample suspension ejected each cycle.

What it is desired to be secured and claimed by Letters Patent of the United States is:

1. In a particle study device having an ejecting means including means for receiving and temporarily storing a given amount of sample, a thermal expansion device mounted within the said receiving and storing means, and means for supplying energy to said thermal expansion device to raise the temperature of said device a predetermined amount to cause said device to expand and increase in volume thereby to eject a specific minute amount of sample from said receiving and storing means, the improvement comprising;
   first means mounted in said thermal expansion device for monitoring said temperature rise, said means having a characteristic which varies with said temperature, and
   second means coupled to said first means and said means for supplying energy and operative in response to said first means having a predetermined characteristic to terminate supply of said energy to said thermal expansion device.

2. The particle studying device of claim 1 wherein said first means include, thermistor means mounted in said thermal expansion device, said thermistor means resistance varying in accordance with the temperature.

3. The particle studying device of claim 1 wherein said second means include,
   supply means coupled to said first means for developing a signal thereat which varies in accordance with said characteristic;
   memory means for storing said signal upon initial application of said energy to said thermal expansion device, and
   comparison means coupled to said first means, said memory means and said means for supplying energy, said comparison means operative in response to a predetermined difference between said memory means signal and said first means signal to terminate the supply of said energy.

4. The particle study device of claim 3 wherein said first means include, thermistor means mounted in said thermal expansion device, said thermistor means resistance varying in accordance with the temperature.

5. The particle study device of claim 4 wherein said supply means include, a source of current coupled to said thermistor means for supplying current thereto, said thermistor means developing a voltage thereacross in response to said current, said voltage varying in accordance with said temperature.

6. The particle study device of claim 5 further including amplifier means coupled to said thermistor means, to said memory means and to said comparison means, said amplifier means being operative to compare said voltage to a reference signal and develop a control signal varying in accordance with variations therebetween.

7. A particle studying device of claim 3 wherein said memory means include, a track and hold circuit coupled to said first means and operative to develop a signal corresponding to the signal received and to maintain the last developed signal upon removal of the received signal.

8. The particle study device of claim 7 wherein said comparison means include, a comparator coupled to said first means and said track and hold circuit and operative in response to a particular difference therebetween to develop a comparison signal, and switch means operative in response to said comparison signal to terminate the supply of energy from said means for supplying energy to said first means.

9. The particle study device of claim 8 further including switch means coupled between said first means and said track and hold circuit, said switch means operative in a first operational mode to couple said first means to said track and hold circuit and operative in a second operational mode to interrupt connection between said first means and said track and hold circuit.

10. The particle study device of claim 9 further including amplifier means coupling said first means to said switch means, said amplifier means being operative to compare said signal developed at said first means to a reference signal and develop a control signal varying in accordance with variations therebetween.

11. The particle study device of claim 10 wherein said first means include thermistor means mounted in said thermal expansion device, said thermistor means resistance varying in accordance with the temperature, said supply means coupled to said thermistor means for supplying current thereto, said thermistor means developing a voltage thereacross in response to said current, said voltage varying in accordance with said temperature.

12. A system for operating an ejecting means having means for receiving and temporarily storing a given amount of fluid sample, a thermal expansion device mounted within said receiving and storing means, said device being operative upon application of energy thereto to raise the temperature thereof causing said device to expand and increase in volume thereby to eject a specific minute amount of sample from said receiving and storing means, said system comprising;

monitoring means mounted in said ejecting means for monitoring said temperature rise, said monitoring means having a characteristic which varies with temperature, a source of energy for application to said device, and control means coupled to said monitoring means and to said source of energy, said control means operative in response to said monitoring means having a predetermined characteristic to terminate the supply of said energy from said source to said thermal expansion device.

13. The system of claim 12 wherein said control means include, supply means coupled to said monitoring means for developing a signal thereat which varies in accordance with said characteristic, memory means selectively coupled to said monitoring means at a first predetermined time for storing said signal, and comparison means coupled to said monitoring means and coupled to said memory means and operative in response to a predetermined difference between said memory means stored signal and said signal from said monitoring means to terminate the supply of said energy.

14. The system of claim 13 further including switch means coupled between said monitoring means and said memory means, said switch means operative in a first operational mode to couple said monitoring means to said memory means and operative in a second operational mode to interrupt the connection between said monitoring means and said memory means.

15. The system of claim 14 wherein said memory means include a track and hold circuit coupled to said switch means and said comparison means, said switch means being operative in said first operational mode to couple said monitoring means to said track and hold circuit and operative in said second operational mode to interrupt connection between said monitoring means and said track and hold circuit.

16. The system of claim 15 wherein said monitoring means include a thermistor mounted in said ejecting means, said supply means being coupled to said thermistor for supplying current thereto, said thermistor developing a voltage thereacross in response to said current which varies in accordance with said temperature and amplifier means coupling said thermistor to said switch means, said amplifier means being operative to compare said thermistor voltage to a reference voltage and to develop a control signal varying in accordance with variations therebetween, said control signal being coupled to said comparison means and said switch means, said switch means coupling said control signal to said track and hold circuit in said first operational mode.

17. The system of claim 16 wherein said switch means is operative upon actuation to switch from said first to said second operational mode.

18. The system of claim 16 wherein said track and hold circuit includes capacitor means coupled to said switch means and operative to receive said control signal and develop a voltage thereacross varying in accordance with said control signal and voltage supply means developing a predetermined voltage thereacross coupled to said capacitor means and said comparison means, said capacitor voltage and said predetermined voltage combining to develop a total voltage, said total voltage being coupled to said comparison means.

19. In a particle study device the combination including an ejecting means including means for receiving and temporarily storing a given amount of sample, a thermal expansion device mounted within said receiving and storing means, and a source of energy coupled to said thermal expansion device to raise the temperature of said device a predetermined amount to cause the device to expand and increase in volume thereby to eject a specific minute amount of sample from said receiving and storing means, monitoring means mounted in said ejecting means for monitoring said temperature rise, said monitoring means having a characteristic which varies with said temperature, and control means coupled to said monitoring means and to said source of energy, said control means operative in response to said monitoring means having a predetermined characteristic to terminate the supply of said energy from said source to said thermal expansion device.

20. A method for ejecting a predetermined amount of sample from an ejecting device having means for receiving and temporarily storing a given amount of sample and a thermal expansion device mounted within said receiving and storing means, said method including the steps of;

monitoring the temperature of said thermal expansion device at a first time and storing said monitor temperature, supplying energy to said thermal expansion device after said first time for raising the temperature of said device to cause said device to expand and increase in volume thereby to eject a specific minute amount of sample from said receiving and storing means, monitoring the temperature rise of said thermal expansion device after said first time, and terminating supply of said energy to said device when said monitored temperature increases to a predetermined temperature.

21. The method of claim 20 wherein said step of terminating supply of said energy includes the steps of comparing said monitored temperature after said first time to said stored monitored temperature and terminating supply of said energy when said monitored temperature increases a predetermined amount above said stored monitored temperature.

22. The method of claim 20 wherein said steps of monitoring the temperature and the temperature rise include the step of monitoring the voltage developed across a network including at least a thermistor mounted in said thermal expansion device, said network resistance and said voltage varying linearly with temperature.

* * * * *